US012667661B2

(12) United States Patent
Zheng et al.

(10) Patent No.: US 12,667,661 B2
(45) Date of Patent: Jun. 30, 2026

(54) INTELLIGENT SYRINGE CHANGING CAPABILITY WITH MULTIPLE SYRINGE SEATS ON AUTOSAMPLER

(71) Applicant: THERMO FINNIGAN LLC, San Jose, CA (US)

(72) Inventors: Xin Zheng, Austin, TX (US); Deven L. Shinholt, Leander, TX (US)

(73) Assignee: Thermo Finnigan LLC, San Jose, CA (US)

( * ) Notice: Subject to any disclaimer, the term of this patent is extended or adjusted under 35 U.S.C. 154(b) by 997 days.

(21) Appl. No.: 17/728,795

(22) Filed: Apr. 25, 2022

(65) Prior Publication Data

US 2023/0338649 A1    Oct. 26, 2023

(51) Int. Cl.
| | |
|---|---|
| *A61M 5/168* | (2006.01) |
| *A61M 5/20* | (2006.01) |
| *G16H 20/17* | (2018.01) |

(52) U.S. Cl.
CPC .......... *A61M 5/16831* (2013.01); *A61M 5/20* (2013.01); *G16H 20/17* (2018.01); *A61M 2005/16863* (2013.01); *A61M 2205/18* (2013.01); *A61M 2205/50* (2013.01)

(58) Field of Classification Search
CPC ..... G16H 20/17; A61M 5/20; A61M 2205/18; A61M 2205/50; A61M 5/16831
See application file for complete search history.

(56) References Cited

U.S. PATENT DOCUMENTS

| | | | |
|---|---|---|---|
| 10,900,938 B2 | 1/2021 | Iovanni et al. | |
| 2021/0181222 A1* | 6/2021 | Otomo | G01N 35/1011 |
| 2023/0012349 A1* | 1/2023 | Gamache | G01N 30/8637 |

FOREIGN PATENT DOCUMENTS

| | | | | |
|---|---|---|---|---|
| CN | 201791197 U | * | 4/2011 | |
| CN | 107192768 A | | 9/2017 | |
| CN | 209372766 U | | 9/2019 | |
| CN | 212932516 U | | 4/2021 | |
| JP | 2019197016 A | | 5/2018 | |
| KR | 101218184 B1 | | 9/2011 | |
| KR | 20170007594 A | * | 1/2017 | G01N 35/10 |
| WO | WO-2014135985 A2 | * | 9/2014 | A61M 5/24 |
| WO | 2021/0111284 A1 | | 6/2021 | |
| WO | WO-2021111285 A1 | | 6/2021 | |

OTHER PUBLICATIONS

"Multifunctional Autosampler Dramatically Improves GC/MS Analysis Productivity" Shimadzu, Jun. 2020.
"Thermo Scientific TriPlus RSH Autosampler Integrated Sampling System" Thermo Fisher Brochure, 2011.

* cited by examiner

*Primary Examiner* — Stephanie E Bloss
*Assistant Examiner* — Diana Hancock

(57) ABSTRACT

Disclosed herein are scientific instrument support systems, as well as related methods, computing devices, and computer-readable media. For example, in some embodiments, a scientific instrument support apparatus includes evaluation logic to identify a first syringe has a bent needle, a bent plunger, a blocked needle, or a stuck plunger; syringe logic to switch from the first syringe to a second syringe; and reporting logic to notify a user of a syringe problem.

18 Claims, 4 Drawing Sheets

3000

COMPUTING DEVICE 4000

PROCESSING DEVICE 4002

BATTERY/POWER 4008

STORAGE DEVICE 4004

DISPLAY DEVICE 4010

INTERFACE DEVICE 4006

OTHER I/O DEVICES 4012

INTELLIGENT SYRINGE CHANGING CAPABILITY WITH MULTIPLE SYRINGE SEATS ON AUTOSAMPLER

BACKGROUND

Scientific instruments may include a complex arrangement of movable components, sensors, input and output ports, energy sources, and consumable components. Failures or changes in any part of this arrangement may result in a "downed" instrument, one that is not able to perform its intended function.

SUMMARY

In a first aspect, a scientific instrument support apparatus can include evaluation logic to identify a first syringe has a bent needle, a bent plunger, a blocked needle, or a stuck plunger; syringe logic to switch from the first syringe to a second syringe; and reporting logic to generate an entry in an event log or notify a user when there is a syringe problem.

In various embodiments of the first aspect, the evaluation logic, the syringe logic, and the reporting logic can be implemented by a common computing device.

In various embodiments of the first aspect, at least one of the evaluation logic, the syringe logic, and the Reporting logic can be implemented by a computing device remote from the scientific instrument.

In various embodiments of the first aspect, at least one of the evaluation logic, the syringe logic, and the Reporting logic can be implemented by a user computing device.

In various embodiments of the first aspect, at least one of the evaluation logic, the syringe logic, and the Reporting logic can be implemented in the scientific instrument.

In various embodiments of the first aspect, the evaluation logic can further detect an injection anomaly based on an evaluation of a chromatographic dataset.

In various embodiments of the first aspect, the evaluation logic can identify the first syringe has a bent needle or a bent plunger based on image data.

In various embodiments of the first aspect, the syringe logic can further repeat an analysis of the sample when a bent needle or a bent plunger is not identified after the injection anomaly is detected.

In various embodiments of the first aspect, the evaluation logic can further includes pausing a sequence of sample analyses when the bent needle, the bent plunger, the blocked needle, or the stuck plunger is identified.

In various embodiments of the first aspect, the syringe logic can further includes performing an initialization routine on the second syringe prior.

In various embodiments of the first aspect, the reporting logic can generate an entry in an event log or can notify the user if the initialization routine fails or produces an error.

In various embodiments of the first aspect, the syringe logic can repeat the analysis of a sample when the initialization routine completes without errors.

In various embodiments of the first aspect, the syringe logic can resume the sequence of sample analyses after the initialization routine completes without errors.

In various embodiments of the first aspect, the evaluation logic can evaluate the chromatographic data set from the repeat analysis for a further injection anomaly.

In various embodiments of the first aspect, the syringe logic can resume the sequence of sample analyses when the evaluation logic does not detect an injection anomaly during the repeat analysis.

In various embodiments of the first aspect, the reporting logic can generate an entry in the event log or can notify the user when an injection anomaly is detected during the repeat analysis.

In a second aspect, a method for scientific instrument support can include identifying a first syringe has a bent needle, a bent plunger, a blocked needle, or a stuck plunger; switching from the first syringe to a second syringe; and generating an entry in an event log or notifying a user of a syringe problem.

In various embodiments of the second aspect, the method can further include detecting an injection anomaly based on an evaluation of a chromatographic dataset.

In various embodiments of the second aspect, the method can further include identifying the first syringe has a bent needle or a bent plunger based on image data.

In various embodiments of the second aspect, the method can further include repeating an analysis of the sample when a bent needle or a bent plunger is not identified after the injection anomaly is detected.

In various embodiments of the second aspect, the method can further include pausing a sequence of sample analyses when the bent needle, the bent plunger, the blocked needle, or the stuck plunger is identified.

In various embodiments of the second aspect, the method can further include performing an initialization routine on the second syringe prior.

In various embodiments of the second aspect, the method can further include generating an entry in an event log or notifying the user when the initialization routine fails or produces an error.

In various embodiments of the second aspect, the method can further include repeating analysis of a sample when the initialization routine completes without errors.

In various embodiments of the second aspect, the method can further include resuming the sequence of sample analyses after the initialization routine completes without errors.

In various embodiments of the second aspect, the method can further include evaluating the chromatographic data set from the repeat analysis for a further injection anomaly.

In various embodiments of the second aspect, the method can further include resuming the sequence of sample analyses when the evaluation logic does not detect an injection anomaly during the repeat analysis.

In various embodiments of the second aspect, the method can further include generating an entry in the event log or notifying the user when an injection anomaly is detected during the repeat analysis.

In various embodiments of the second aspect, one or more non-transitory computer readable media can have instructions thereon that, when executed by one or more processing devices of a scientific instrument support apparatus, cause the scientific instrument support apparatus to perform the method of the second aspect.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, not by way of limitation, in the figures of the accompanying drawings.

DETAILED DESCRIPTION

Figure 1:
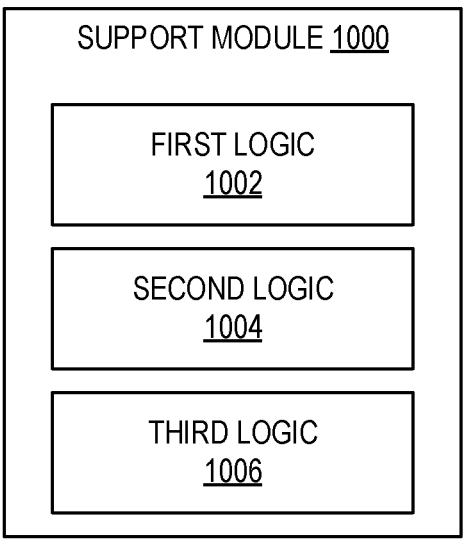
FIG. 1 is a block diagram of an example scientific instrument support module for performing support operations, in accordance with various embodiments.

Disclosed herein are scientific instrument support systems, as well as related methods, computing devices, and computer-readable media. For example, in some embodiments, A scientific instrument support apparatus, comprising evaluation logic to identify a first syringe has a bent needle, a bent plunger, a blocked needle, or a stuck plunger; syringe logic to switch from the first syringe to a second syringe; and reporting logic to notify a user of a syringe problem.

The scientific instrument support embodiments disclosed herein may achieve improved performance relative to conventional approaches. For example, the automatic detection of a syringe problem and switching to an alternate syringe without user intervention can improve system utilization by reducing downtime associated with syringe malfunctions. Additionally, the automatic recovery from a syringe problem reduces the risk of wasted instrument time and reagents from an undetected syringe malfunction when operating the system unattended for extended periods. The embodiments disclosed herein thus provide improvements to scientific instrument technology (e.g., improvements in the computer technology supporting such scientific instruments, among other improvements).

The embodiments disclosed herein may achieve improved reliability and data collection and higher throughput relative to conventional approaches. For example, conventional approaches rely upon user intervention to detect and mitigate the syringe malfunction. However, these approaches suffer from a number of technical problems and limitations, including multiple unusable datasets being collected for samples the instrument attempts to analyze after the syringe malfunction, wasting both instrument time and reagents. Conventional approaches can lead to decreased laboratory throughput if the syringe malfunction cannot be detected and corrected when it occurs.

Various ones of the embodiments disclosed herein may improve upon conventional approaches to achieve the technical advantages of higher throughput and improved data quality by reducing attempts to analyze samples when there is a syringe malfunction and automatically switching to an alternate syringe to correct the syringe malfunction. Such technical advantages are not achievable by routine and conventional approaches, and all users of systems including such embodiments may benefit from these advantages. The technical features of the embodiments disclosed herein are thus decidedly unconventional in the field of autosamplers, as are the combinations of the features of the embodiments disclosed herein. The computational disclosed herein do not only involve the collection and comparison of information but apply new analytical and technical techniques to change the operation of the autosampler. The present disclosure thus introduces functionality that neither a conventional computing device, nor a human, could perform.

Accordingly, the embodiments of the present disclosure may serve any of a number of technical purposes, such as controlling a specific technical system or process; determining from measurements how to control a machine; digital image analysis; identifying a vaccine candidate (e.g., based on a phylogenetic tree); or providing a medical diagnosis by an automated system processing physiological measurements. In particular, the present disclosure provides technical solutions to technical problems, including but not limited to detecting and recovering from syringe malfunctions in an autosampler.

The embodiments disclosed herein thus provide improvements to autosampler technology (e.g., improvements in the computer technology supporting autosamplers, among other improvements).

In the following detailed description, reference is made to the accompanying drawings that form a part hereof wherein like numerals designate like parts throughout, and in which is shown, by way of illustration, embodiments that may be practiced. It is to be understood that other embodiments may be utilized, and structural or logical changes may be made, without departing from the scope of the present disclosure. Therefore, the following detailed description is not to be taken in a limiting sense.

Various operations may be described as multiple discrete actions or operations in turn, in a manner that is most helpful in understanding the subject matter disclosed herein. However, the order of description should not be construed as to imply that these operations are necessarily order dependent. In particular, these operations may not be performed in the order of presentation. Operations described may be performed in a different order from the described embodiment. Various additional operations may be performed, and/or described operations may be omitted in additional embodiments.

For the purposes of the present disclosure, the phrases "A and/or B" and "A or B" mean (A), (B), or (A and B). For the purposes of the present disclosure, the phrases "A, B, and/or C" and "A, B, or C" mean (A), (B), (C), (A and B), (A and C), (B and C), or (A, B, and C). Although some elements may be referred to in the singular (e.g., "a processing device"), any appropriate elements may be represented by multiple instances of that element, and vice versa. For example, a set of operations described as performed by a processing device may be implemented with different ones of the operations performed by different processing devices.

The description uses the phrases "an embodiment," "various embodiments," and "some embodiments," each of which may refer to one or more of the same or different embodiments. Furthermore, the terms "comprising," "including," "having," and the like, as used with respect to embodiments of the present disclosure, are synonymous. When used to describe a range of dimensions, the phrase "between X and Y" represents a range that includes X and Y. As used herein, an "apparatus" may refer to any individual device, collection of devices, part of a device, or collections of parts of devices. The drawings are not necessarily to scale.

FIG. 1 is a block diagram of a scientific instrument support module 1000 for performing support operations, in accordance with various embodiments. The scientific instrument support module 1000 may be implemented by circuitry (e.g., including electrical and/or optical components), such as a programmed computing device. The logic of the scientific instrument support module 1000 may be included in a single computing device or may be distributed across multiple computing devices that are in communication with each other as appropriate. Examples of computing devices that may, singly or in combination, implement the scientific instrument support module 1000 are discussed herein with reference to the computing device 4000 of FIG. 4, and examples of systems of interconnected computing devices, in which the scientific instrument support module 1000 may be implemented across one or more of the computing devices, is discussed herein with reference to the scientific instrument support system 5000 of FIG. 5.

The scientific instrument support module 1000 may include first logic 1002, second logic 1004, and third logic 1006. As used herein, the term "logic" may include an apparatus that is to perform a set of operations associated with the logic. For example, any of the logic elements included in the support module 1000 may be implemented by one or more computing devices programmed with instructions to cause one or more processing devices of the computing devices to perform the associated set of operations. In a particular embodiment, a logic element may include one or more non-transitory computer-readable media having instructions thereon that, when executed by one or more processing devices of one or more computing devices, cause the one or more computing devices to perform the associated set of operations. As used herein, the term "module" may refer to a collection of one or more logic elements that, together, perform a function associated with the module. Different ones of the logic elements in a module may take the same form or may take different forms. For example, some logic in a module may be implemented by a programmed general-purpose processing device, while other logic in a module may be implemented by an application-specific integrated circuit (ASIC). In another example, different ones of the logic elements in a module may be associated with different sets of instructions executed by one or more processing devices. A module may not include all of the logic elements depicted in the associated drawing; for example, a module may include a subset of the logic elements depicted in the associated drawing when that module is to perform a subset of the operations discussed herein with reference to that module.

The first logic 1002 may detect injection anomalies during analysis of a sample and identify a bent needle or plunger, a blocked needle, or a stuck plunger. In various embodiment, the first logic 1002 may detect injection anomalies by obtaining a chromatogram and determining if the chromatogram is representative of a successful result or if a problem such as a missed injection occurred. In various embodiments, when a missed injection occurs, the first logic can use image data to determine the cause of the missed injection such as by using image data to detect a bent needle or plunger, a blocked needle, or a stuck plunger.

In various embodiments, the first logic 1002 can instruct the scientific instrument to process a sample, such as by using an autosampler to take an aliquot from a sample vial, inject the aliquot onto a chromatography column, elute the components of the sample from the column, and use an analyzer to collect data on the components of the sample. First logic 1002 can further receive the data from the analyzer and store the data into a database, filesystem, or the like for further processing.

In various embodiments, first logic 1002 can include calculating an intensity score for the chromatogram and comparing the score to a threshold. Alternatively, first logic 1002 can apply a machine learning model to the chromatogram to classify the chromatogram as successful or abnormal.

In various embodiments, the first logic 1002 can instruct an image capture device to capture an image of the syringe and analyze the image data to determine if the needle or plunger is bent or misaligned. In various embodiments, first logic 1002 can analyze the image data to identify the location of the tip of the needle within the image, such as by pattern matching. Additionally, first logic 1002 can determine if the tip location is inside or outside of an acceptable area of the image. Alternatively, first logic 1002 can apply a machine learning model to the image data to classify the needle or plunger as bent or not bent.

The second logic 1004 may switch to an alternate syringe, perform a syringe precheck, and repeat an analysis of a sample.

In various embodiments, second logic 1004 may instruct an autosampler to rotate a syringe holder from a first position in which the bent syringe is in an active location to a second position in which an alternate syringe is in the active location. Alternatively, the second logic 1004 may instruct the autosampler to place the bent syringe in an empty location on a syringe rack and grab the alternate syringe from another location on a syringe rack.

In various embodiments, second logic 1004 may instruct the autosampler to perform a self-alignment check of the alternate syringe on an injection port, sample vials, and wash vials. The second logic 1004 may also instruct the autosampler to perform a calibration on the syringe, such as by finding the zero point for the syringe plunger and finding a bottom out position of the syringe needle. The second logic 1004 may also instruct the autosampler to perform a vial check to ensure there are no missing or misaligned vials.

The third logic 1006 may notify a user and/or log a syringe problem, such as within a secure audit trail. In various embodiments, the third logic 1006 may log the detection of an anomaly and corrective actions taken, and if operation was successfully restored or not. In various embodiments, the third logic 1006 may send a message, such as an email, a push message, a text message, or other forms of electronic communication to the user to notify them of the detected problem. In various embodiments, the third logic 1006 may send a message to the user if operation is not successfully restored. The third logic 1006 can also track the number of available alternate syringes and notify the user when the number of available alternate syringes is low so the user can replace malfunctioning syringes that have been removed from operation with new syringes such that more alternate syringes are available.

In various embodiments, the third logic 1006 can also suggest the user order replacement syringes via an ecommerce site or even automatically order the replacement syringes. In some embodiments, the third logic 1006 may track the number of times syringes are replaced across one or more instruments. In other embodiments, the third logic may communication with an inventory tracking system to determine the number of syringes available in current inventory.

Figure 2:
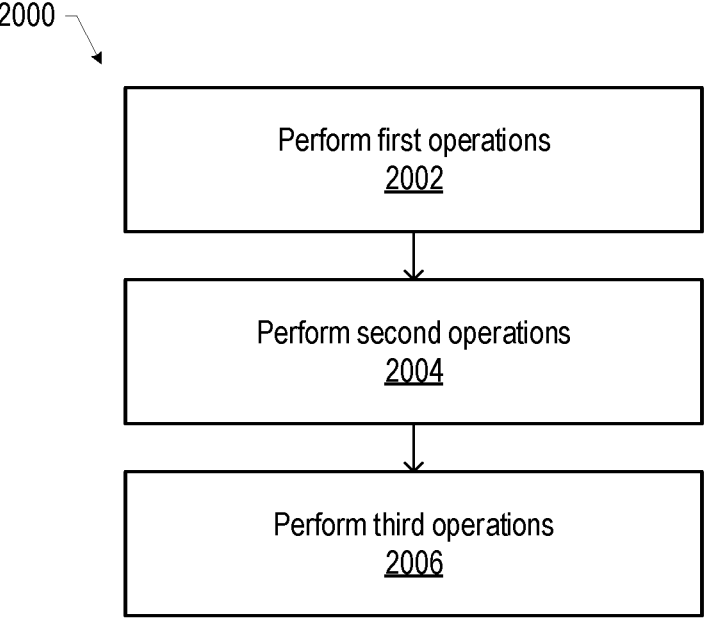
FIG. 2 is a flow diagram of an example method of performing support operations, in accordance with various embodiments.

FIG. 2 is a flow diagram of a method 2000 of performing support operations, in accordance with various embodiments. Although the operations of the method 2000 may be illustrated with reference to particular embodiments disclosed herein (e.g., the scientific instrument support modules 1000 discussed herein with reference to FIG. 1, the GUI 3000 discussed herein with reference to FIG. 3, the computing devices 4000 discussed herein with reference to FIG. 4, and/or the scientific instrument support system 5000 discussed herein with reference to FIG. 5), the method 2000 may be used in any suitable setting to perform any suitable support operations. Operations are illustrated once each and in a particular order in FIG. 2, but the operations may be reordered and/or repeated as desired and appropriate (e.g., different operations performed may be performed in parallel, as suitable).

At 2002, first operations may be performed. For example, the first logic 1002 of a support module 1000 may perform the operations of 2002. The first operations may include detecting injection anomalies during analysis of a sample and identify bent needles or bent plungers using image data of the syringe. In various embodiment, the first operations may detect injection anomalies by obtaining a chromatogram and determining if the chromatogram is representative of a successful result or if a problem such as a missed injection occurred.

In various embodiments, the first operations can include instructing the scientific instrument to process a sample, such as by using an autosampler to take an aliquot from a sample vial, inject the aliquot onto a chromatography column, elute the components of the sample from the column, and use an analyzer to collect data on the components of the sample. The first operations can further receive the data from the analyzer and store the data into a database, filesystem, or the like for further processing.

In various embodiments, the first operations can include calculating an intensity score for the chromatogram and comparing the score to a threshold. Alternatively, first operations can apply a machine learning model to the chromatogram to classify the chromatogram as successful or abnormal.

In various embodiments, the first operations can include instructing an image capture device to capture an image of the syringe and analyze the image data to determine if the needle or plunger is bent or misaligned. In various embodiments, first operations can analyze the image data to identify the location of the tip of the needle within the image, such as by pattern matching, and determine if the tip location is inside or outside of an acceptable area of the image. Alternatively, the first operations can apply a machine learning model to the image data to classify the needle as bent or not bent.

At 2004, second operations may be performed. For example, the second logic 1004 of a support module 1000 may perform the operations of 2004. The second operations may include switching to an alternate syringe, performing a syringe precheck, and repeat an analysis of the sample.

In various embodiments, second operations may include instructing an autosampler to rotate a syringe holder from a first position in which the damaged syringe is in an active location to a second position in which an alternate syringe is in the active location. Alternatively, the second logic 1004 may instruct the autosampler to place the damaged syringe in an empty location on a syringe rack and grab the alternate syringe from another location on a syringe rack.

In various embodiments, the second operations may instruct the autosampler to perform a self-alignment check of the alternate syringe on an injection port, sample vials, and wash vials. The second operations may also instruct the autosampler to perform a calibration on the syringe, such as by finding the zero point for the syringe plunger and finding a bottom out position of the syringe needle. The second operations may also instruct the autosampler to perform a vial check to ensure there are no missing vials.

At 2006, third operations may be performed. For example, the third logic 1006 of a support module 1000 may perform the operations of 2006. The third operations may include notifying a user and/or logging a syringe problem. In various embodiments, the third operations may log the detection of an anomaly and corrective actions taken, and if operation was successfully restored or not. In various embodiments, the third operations may send a message, such as an email, a push message, a text message, other forms of electronic communication, or any combination thereof, to the user to notify the user of the detected problem. In various embodiments, the third operations may send a message to the user if operation is not successfully restored. The third operations can also track the number of available alternate syringes and notify the user when the number of available alternate syringes is low so the user can replace malfunctioning syringes that have been removed from operation with new syringes such that more alternate syringes are available.

Figure 4:
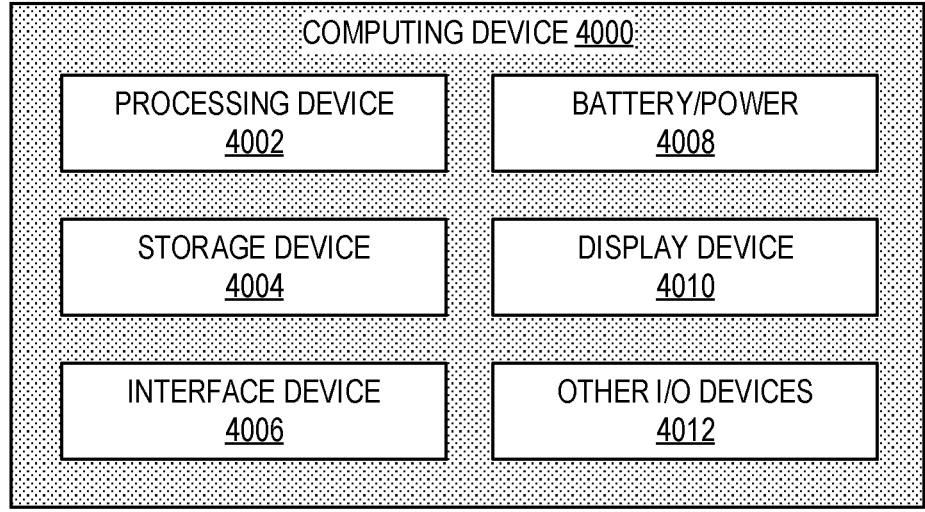
FIG. 4 is a block diagram of an example computing device that may perform some or all of the scientific instrument support methods disclosed herein, in accordance with various embodiments.
Figure 5:
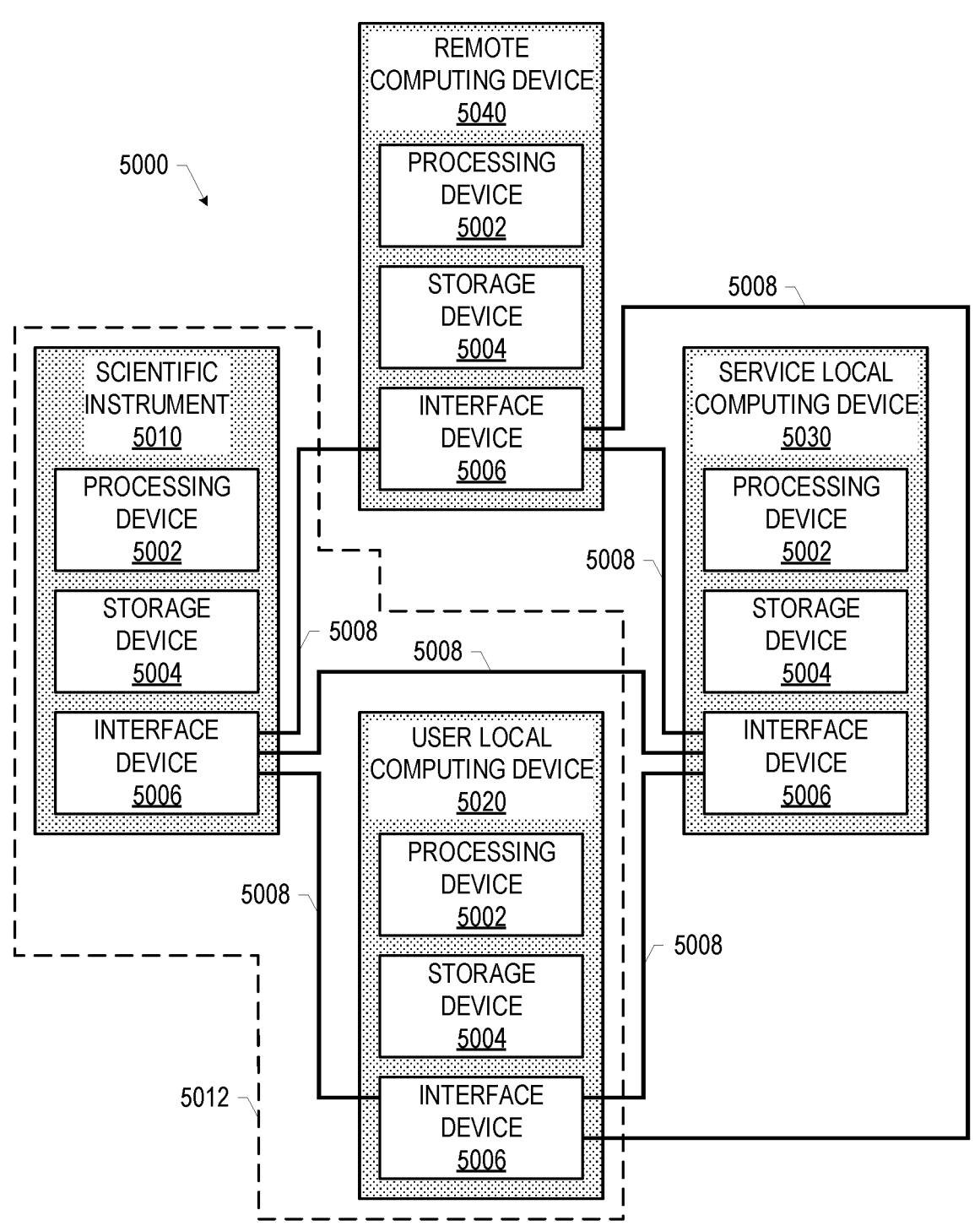
FIG. 5 is a block diagram of an example scientific instrument support system in which some or all of the scientific instrument support methods disclosed herein may be performed, in accordance with various embodiments.

The scientific instrument support methods disclosed herein may include interactions with a human user (e.g., via the user local computing device 5020 discussed herein with reference to FIG. 5). These interactions may include providing information to the user (e.g., information regarding the operation of a scientific instrument such as the scientific instrument 5010 of FIG. 5, information regarding a sample being analyzed or other test or measurement performed by a scientific instrument, information retrieved from a local or remote database, or other information) or providing an option for a user to input commands (e.g., to control the operation of a scientific instrument such as the scientific instrument 5010 of FIG. 5, or to control the analysis of data generated by a scientific instrument), queries (e.g., to a local or remote database), or other information. In some embodiments, these interactions may be performed through a graphical user interface (GUI) that includes a visual display on a display device (e.g., the display device 4010 discussed herein with reference to FIG. 4) that provides outputs to the user and/or prompts the user to provide inputs (e.g., via one or more input devices, such as a keyboard, mouse, trackpad, or touchscreen, included in the other I/O devices 4012 discussed herein with reference to FIG. 4). The scientific instrument support systems disclosed herein may include any suitable GUIs for interaction with a user.

Figure 3:
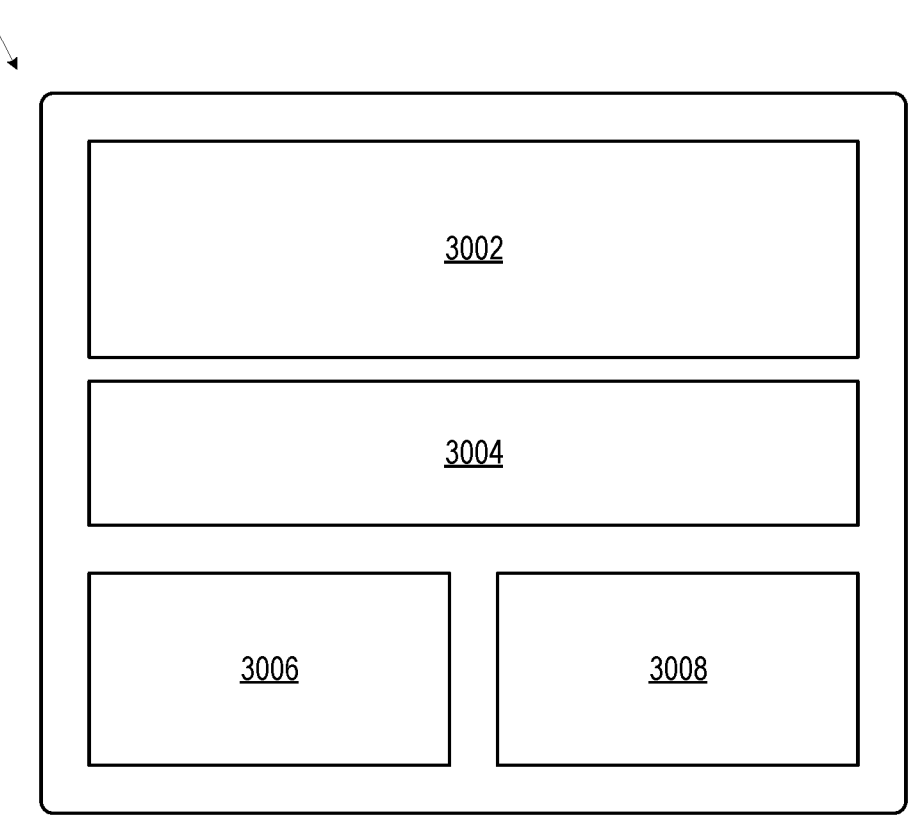
FIG. 3 is an example of a graphical user interface that may be used in the performance of some or all of the support methods disclosed herein, in accordance with various embodiments.

FIG. 3 depicts an example GUI 3000 that may be used in the performance of some or all of the support methods disclosed herein, in accordance with various embodiments. As noted above, the GUI 3000 may be provided on a display device (e.g., the display device 4010 discussed herein with reference to FIG. 4) of a computing device (e.g., the computing device 4000 discussed herein with reference to FIG. 4) of a scientific instrument support system (e.g., the scientific instrument support system 5000 discussed herein with reference to FIG. 5), and a user may interact with the GUI 3000 using any suitable input device (e.g., any of the input devices included in the other I/O devices 4012 discussed herein with reference to FIG. 4) and input technique (e.g., movement of a cursor, motion capture, facial recognition, gesture detection, voice recognition, actuation of buttons, etc.).

The GUI 3000 may include a data display region 3002, a data analysis region 3004, a scientific instrument control region 3006, and a settings region 3008. The particular number and arrangement of regions depicted in FIG. 3 is simply illustrative, and any number and arrangement of regions, including any desired features, may be included in a GUI 3000.

The data display region 3002 may display data generated by a scientific instrument (e.g., the scientific instrument 5010 discussed herein with reference to FIG. 5). For example, the data display region 3002 may display chromatography data collected on a sample. Additionally, the data display region 3002 may provide a visual indication that the chromatography data is indicative of an injection anomaly.

The data analysis region 3004 may display the results of data analysis (e.g., the results of analyzing the data illustrated in the data display region 3002 and/or other data). For example, the data analysis region 3004 may display chromatographic information, such as retention time and intensity of peaks in the chromatographic data. In some embodiments, the data display region 3002 and the data analysis region 3004 may be combined in the GUI 3000 (e.g., to include data output from a scientific instrument, and some analysis of the data, in a common graph or region).

The scientific instrument control region 3006 may include options that allow the user to control a scientific instrument (e.g., the scientific instrument 5010 discussed herein with reference to FIG. 5). For example, the scientific instrument control region 3006 may include settings to configure the syringe switching operation. The scientific instrument control region 3006 may also include an interface to indicate the status of syringe locations, including which locations are empty, which locations include alternate syringes, and which locations include malfunctioning syringes that need to be replaced. In various embodiments, the instrument can be configured to utilize multiple types of syringes and the configuration of the syringe swapping operation can include grouping syringe locations by type of syringe such that a malfunctioning syringe can be replaced by a similar syringe and that multiple types of syringes can have alternate or backup syringes available.

The settings region 3008 may include options that allow the user to control the features and functions of the GUI 3000 (and/or other GUIs) and/or perform common computing operations with respect to the data display region 3002 and data analysis region 3004 (e.g., saving data on a storage device, such as the storage device 4004 discussed herein with reference to FIG. 4, sending data to another user, labeling data, etc.). For example, the settings region 3008 may include notification settings to configure when and how syringe events are logged and when and how messages are sent to the user. For example, the settings region 3008 can include options to log and/or notify when a syringe malfunction is detected, when a syringe is replaced, when the sequence is resumed, when the replacement syringe does not pass the syringe precheck, and the like. Additionally, settings region 3008 can include options for how to notify the user as well which can include configuration of an email or phone number depending on the type of notification sent to the user.

As noted above, the scientific instrument support module 1000 may be implemented by one or more computing devices. FIG. 4 is a block diagram of a computing device 4000 that may perform some or all of the scientific instrument support methods disclosed herein, in accordance with various embodiments. In some embodiments, the scientific instrument support module 1000 may be implemented by a single computing device 4000 or by multiple computing devices 4000. Further, as discussed below, a computing device 4000 (or multiple computing devices 4000) that implements the scientific instrument support module 1000 may be part of one or more of the scientific instrument 5010, the user local computing device 5020, the service local computing device 5030, or the remote computing device 5040 of FIG. 5.

The computing device 4000 of FIG. 4 is illustrated as having a number of components, but any one or more of these components may be omitted or duplicated, as suitable for the application and setting. In some embodiments, some or all of the components included in the computing device 4000 may be attached to one or more motherboards and enclosed in a housing (e.g., including plastic, metal, and/or other materials). In some embodiments, some these components may be fabricated onto a single system-on-a-chip (SoC) (e.g., an SoC may include one or more processing devices 4002 and one or more storage devices 4004). Additionally, in various embodiments, the computing device 4000 may not include one or more of the components illustrated in FIG. 4, but may include interface circuitry (not shown) for coupling to the one or more components using any suitable interface (e.g., a Universal Serial Bus (USB) interface, a High-Definition Multimedia Interface (HDMI) interface, a Controller Area Network (CAN) interface, a Serial Peripheral Interface (SPI) interface, an Ethernet interface, a wireless interface, or any other appropriate interface). For example, the computing device 4000 may not include a display device 4010, but may include display device interface circuitry (e.g., a connector and driver circuitry) to which a display device 4010 may be coupled.

The computing device 4000 may include a processing device 4002 (e.g., one or more processing devices). As used herein, the term "processing device" may refer to any device or portion of a device that processes electronic data from registers and/or memory to transform that electronic data into other electronic data that may be stored in registers and/or memory. The processing device 4002 may include one or more digital signal processors (DSPs), application-specific integrated circuits (ASICs), central processing units (CPUs), graphics processing units (GPUs), cryptoprocessors (specialized processors that execute cryptographic algorithms within hardware), server processors, or any other suitable processing devices.

The computing device 4000 may include a storage device 4004 (e.g., one or more storage devices). The storage device 4004 may include one or more memory devices such as random access memory (RAM) (e.g., static RAM (SRAM) devices, magnetic RAM (MRAM) devices, dynamic RAM (DRAM) devices, resistive RAM (RRAM) devices, or conductive-bridging RAM (CBRAM) devices), hard drive-based memory devices, solid-state memory devices, networked drives, cloud drives, or any combination of memory devices. In some embodiments, the storage device 4004 may include memory that shares a die with a processing device 4002. In such an embodiment, the memory may be used as cache memory and may include embedded dynamic random access memory (eDRAM) or spin transfer torque magnetic random access memory (STT-MRAM), for example. In some embodiments, the storage device 4004 may include non-transitory computer readable media having instructions thereon that, when executed by one or more processing devices (e.g., the processing device 4002), cause the computing device 4000 to perform any appropriate ones of or portions of the methods disclosed herein.

The computing device 4000 may include an interface device 4006 (e.g., one or more interface devices 4006). The interface device 4006 may include one or more communication chips, connectors, and/or other hardware and software to govern communications between the computing device 4000 and other computing devices. For example, the interface device 4006 may include circuitry for managing wireless communications for the transfer of data to and from the computing device 4000. The term "wireless" and its derivatives may be used to describe circuits, devices, systems, methods, techniques, communications channels, etc., that may communicate data through the use of modulated electromagnetic radiation through a nonsolid medium. The term does not imply that the associated devices do not contain any wires, although in some embodiments they might not. Circuitry included in the interface device 4006 for managing wireless communications may implement any of a number of wireless standards or protocols, including but not limited to Institute for Electrical and Electronic Engineers (IEEE) standards including Wi-Fi (IEEE 802.11 family), IEEE 802.16 standards (e.g., IEEE 802.16-2005 Amendment), Long-Term Evolution (LTE) project along with any amendments, updates, and/or revisions (e.g., advanced LTE project, ultra mobile broadband (UMB) project (also referred to as "3GPP2"), etc.). In some embodiments, circuitry included in the interface device 4006 for managing wireless communications may operate in accordance with a Global System for Mobile Communication (GSM), General Packet Radio Service (GPRS), Universal Mobile Telecommunications System (UMTS), High Speed Packet Access (HSPA), Evolved HSPA (E-HSPA), or LTE network. In some embodiments, circuitry included in the interface device 4006 for managing wireless communications may operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). In some embodiments, circuitry included in the interface device 4006 for managing wireless communications may operate in accordance with Code Division Multiple Access (CDMA), Time Division Multiple Access (TDMA), Digital Enhanced Cordless Telecommunications (DECT), Evolution-Data Optimized (EV-DO), and derivatives thereof, as well as any other wireless protocols that are designated as 3G, 4G, 5G, and beyond. In some embodiments, the interface device 4006 may include one or more antennas (e.g., one or more antenna arrays) to receipt and/or transmission of wireless communications.

In some embodiments, the interface device 4006 may include circuitry for managing wired communications, such as electrical, optical, or any other suitable communication protocols. For example, the interface device 4006 may include circuitry to support communications in accordance with Ethernet technologies. In some embodiments, the interface device 4006 may support both wireless and wired communication, and/or may support multiple wired communication protocols and/or multiple wireless communication protocols. For example, a first set of circuitry of the interface device 4006 may be dedicated to shorter-range wireless communications such as Wi-Fi or Bluetooth, and a second set of circuitry of the interface device 4006 may be dedicated to longer-range wireless communications such as global positioning system (GPS), EDGE, GPRS, CDMA, WiMAX, LTE, EV-DO, or others. In some embodiments, a first set of circuitry of the interface device 4006 may be dedicated to wireless communications, and a second set of circuitry of the interface device 4006 may be dedicated to wired communications.

The computing device 4000 may include battery/power circuitry 4008. The battery/power circuitry 4008 may include one or more energy storage devices (e.g., batteries or capacitors) and/or circuitry for coupling components of the computing device 4000 to an energy source separate from the computing device 4000 (e.g., AC line power).

The computing device 4000 may include a display device 4010 (e.g., multiple display devices). The display device 4010 may include any visual indicators, such as a heads-up display, a computer monitor, a projector, a touchscreen display, a liquid crystal display (LCD), a light-emitting diode display, or a flat panel display.

The computing device 4000 may include other input/output (I/O) devices 4012. The other I/O devices 4012 may include one or more audio output devices (e.g., speakers, headsets, earbuds, alarms, etc.), one or more audio input devices (e.g., microphones or microphone arrays), location devices (e.g., GPS devices in communication with a satellite-based system to receive a location of the computing device 4000, as known in the art), audio codecs, video codecs, printers, sensors (e.g., thermocouples or other temperature sensors, humidity sensors, pressure sensors, vibration sensors, accelerometers, gyroscopes, etc.), image capture devices such as cameras, keyboards, cursor control devices such as a mouse, a stylus, a trackball, or a touchpad, bar code readers, Quick Response (QR) code readers, or radio frequency identification (RFID) readers, for example.

The computing device 4000 may have any suitable form factor for its application and setting, such as a handheld or mobile computing device (e.g., a cell phone, a smart phone, a mobile internet device, a tablet computer, a laptop computer, a netbook computer, an ultrabook computer, a personal digital assistant (PDA), an ultra mobile personal computer, etc.), a desktop computing device, or a server computing device or other networked computing component.

One or more computing devices implementing any of the scientific instrument support modules or methods disclosed herein may be part of a scientific instrument support system. FIG. 5 is a block diagram of an example scientific instrument support system 5000 in which some or all of the scientific instrument support methods disclosed herein may be performed, in accordance with various embodiments. The scientific instrument support modules and methods disclosed herein (e.g., the scientific instrument support module 1000 of FIG. 1 and the method 2000 of FIG. 2) may be implemented by one or more of the scientific instrument 5010, the user local computing device 5020, the service local computing device 5030, or the remote computing device 5040 of the scientific instrument support system 5000.

Any of the scientific instrument 5010, the user local computing device 5020, the service local computing device 5030, or the remote computing device 5040 may include any of the embodiments of the computing device 4000 discussed herein with reference to FIG. 4, and any of the scientific instrument 5010, the user local computing device 5020, the service local computing device 5030, or the remote computing device 5040 may take the form of any appropriate ones of the embodiments of the computing device 4000 discussed herein with reference to FIG. 4.

The scientific instrument 5010, the user local computing device 5020, the service local computing device 5030, or the remote computing device 5040 may each include a processing device 5002, a storage device 5004, and an interface device 5006. The processing device 5002 may take any suitable form, including the form of any of the processing devices 4002 discussed herein with reference to FIG. 4, and the processing devices 5002 included in different ones of the scientific instrument 5010, the user local computing device 5020, the service local computing device 5030, or the remote computing device 5040 may take the same form or different forms. The storage device 5004 may take any suitable form, including the form of any of the storage devices 5004 discussed herein with reference to FIG. 4, and the storage devices 5004 included in different ones of the scientific instrument 5010, the user local computing device 5020, the service local computing device 5030, or the remote computing device 5040 may take the same form or different forms. The interface device 5006 may take any suitable form, including the form of any of the interface devices 4006 discussed herein with reference to FIG. 4, and the interface devices 5006 included in different ones of the scientific instrument 5010, the user local computing device 5020, the service local computing device 5030, or the remote computing device 5040 may take the same form or different forms.

The scientific instrument 5010, the user local computing device 5020, the service local computing device 5030, and the remote computing device 5040 may be in communication with other elements of the scientific instrument support system 5000 via communication pathways 5008. The communication pathways 5008 may communicatively couple the interface devices 5006 of different ones of the elements of the scientific instrument support system 5000, as shown, and may be wired or wireless communication pathways (e.g., in accordance with any of the communication techniques discussed herein with reference to the interface devices 4006 of the computing device 4000 of FIG. 4). The particular scientific instrument support system 5000 depicted in FIG. 5 includes communication pathways between each pair of the scientific instrument 5010, the user local computing device 5020, the service local computing device 5030, and the remote computing device 5040, but this "fully connected" implementation is simply illustrative, and in various embodiments, various ones of the communication pathways 5008 may be absent. For example, in some embodiments, a service local computing device 5030 may not have a direct communication pathway 5008 between its interface device 5006 and the interface device 5006 of the scientific instrument 5010, but may instead communicate with the scientific instrument 5010 via the communication pathway 5008 between the service local computing device 5030 and the user local computing device 5020 and the communication pathway 5008 between the user local computing device 5020 and the scientific instrument 5010.

The scientific instrument 5010 may include any appropriate scientific instrument, such as a chromatography system, a mass spectrometer system, or a chromatography-mass spectrometer system. The chromatography system can include a gas chromatography system, a liquid chromatography system, an ion chromatography system, or any other chromatography system that can utilize an autosampler. The mass spectrometry system can include an ionization source that allows direct injection of a sample by an autosampler. The chromatography-mass spectrometry can be of any type chromatography that can utilize an autosampler to supply samples and provide the output of the chromatographic column to the mass spectrometer.

The user local computing device 5020 may be a computing device (e.g., in accordance with any of the embodiments of the computing device 4000 discussed herein) that is local to a user of the scientific instrument 5010. In some embodiments, the user local computing device 5020 may also be local to the scientific instrument 5010, but this need not be the case; for example, a user local computing device 5020 that is in a user's home or office may be remote from, but in communication with, the scientific instrument 5010 so that the user may use the user local computing device 5020 to control and/or access data from the scientific instrument 5010. In some embodiments, the user local computing device 5020 may be a laptop, smartphone, or tablet device. In some embodiments the user local computing device 5020 may be a portable computing device. In some embodiments, the user local computing device 5020 may receive notifications of injection anomalies and syringe swap events.

The service local computing device 5030 may be a computing device (e.g., in accordance with any of the embodiments of the computing device 4000 discussed herein) that is local to an entity that services the scientific instrument 5010. For example, the service local computing device 5030 may be local to a manufacturer of the scientific instrument 5010 or to a third-party service company. In some embodiments, the service local computing device 5030 may communicate with the scientific instrument 5010, the user local computing device 5020, and/or the remote computing device 5040 (e.g., via a direct communication pathway 5008 or via multiple "indirect" communication pathways 5008, as discussed above) to receive data regarding the operation of the scientific instrument 5010, the user local computing device 5020, and/or the remote computing device 5040 (e.g., the results of self-tests of the scientific instrument 5010, calibration coefficients used by the scientific instrument 5010, the measurements of sensors associated with the scientific instrument 5010, etc.). In some embodiments, the service local computing device 5030 may communicate with the scientific instrument 5010, the user local computing device 5020, and/or the remote computing device 5040 (e.g., via a direct communication pathway 5008 or via multiple "indirect" communication pathways 5008, as discussed above) to transmit data to the scientific instrument 5010, the user local computing device 5020, and/or the remote computing device 5040 (e.g., to update programmed instructions, such as firmware, in the scientific instrument 5010, to initiate the performance of test or calibration sequences in the scientific instrument 5010, to update programmed instructions, such as software, in the user local computing device 5020 or the remote computing device 5040, etc.). A user of the scientific instrument 5010 may utilize the scientific instrument 5010 or the user local computing device 5020 to communicate with the service local computing device 5030 to report a problem with the scientific instrument 5010 or the user local computing device 5020, to request a visit from a technician to improve the operation of the scientific instrument 5010, to order consumables or replacement parts associated with the scientific instrument 5010, or for other purposes.

The remote computing device 5040 may be a computing device (e.g., in accordance with any of the embodiments of the computing device 4000 discussed herein) that is remote from the scientific instrument 5010 and/or from the user local computing device 5020. In some embodiments, the remote computing device 5040 may be included in a datacenter or other large-scale server environment. In some embodiments, the remote computing device 5040 may include network-attached storage (e.g., as part of the storage device 5004). The remote computing device 5040 may store data generated by the scientific instrument 5010, perform analyses of the data generated by the scientific instrument 5010 (e.g., in accordance with programmed instructions), facilitate communication between the user local computing device 5020 and the scientific instrument 5010, and/or facilitate communication between the service local computing device 5030 and the scientific instrument 5010.

In some embodiments, one or more of the elements of the scientific instrument support system 5000 illustrated in FIG. 5 may not be present. Further, in some embodiments, multiple ones of various ones of the elements of the scientific instrument support system 5000 of FIG. 5 may be present. For example, a scientific instrument support system 5000 may include multiple user local computing devices 5020 (e.g., different user local computing devices 5020 associated with different users or in different locations). In another example, a scientific instrument support system 5000 may include multiple scientific instruments 5010, all in communication with service local computing device 5030 and/or a remote computing device 5040; in such an embodiment, the service local computing device 5030 may monitor these multiple scientific instruments 5010, and the service local computing device 5030 may cause updates or other information may be "broadcast" to multiple scientific instruments 5010 at the same time. Different ones of the scientific instruments 5010 in a scientific instrument support system 5000 may be located close to one another (e.g., in the same room) or farther from one another (e.g., on different floors of a building, in different buildings, in different cities, etc.). In some embodiments, a scientific instrument 5010 may be connected to an Internet-of-Things (IoT) stack that allows for command and control of the scientific instrument 5010 through a web-based application, a virtual or augmented reality application, a mobile application, and/or a desktop application. Any of these applications may be accessed by a user operating the user local computing device 5020 in communication with the scientific instrument 5010 by the intervening remote computing device 5040. In some embodiments, a scientific instrument 5010 may be sold by the manufacturer along with one or more associated user local computing devices 5020 as part of a local scientific instrument computing unit 5012.

In some embodiments, different ones of the scientific instruments 5010 included in a scientific instrument support system 5000 may be different types of scientific instruments 5010; for example, one scientific instrument 5010 may be a gas chromatography-mass spectrometry system, while another scientific instrument 5010 may be a liquid chromatography-mass spectrometry system. In some such embodiments, the remote computing device 5040 and/or the user local computing device 5020 may combine data from different types of scientific instruments 5010 included in a scientific instrument support system 5000.

Figure 6:
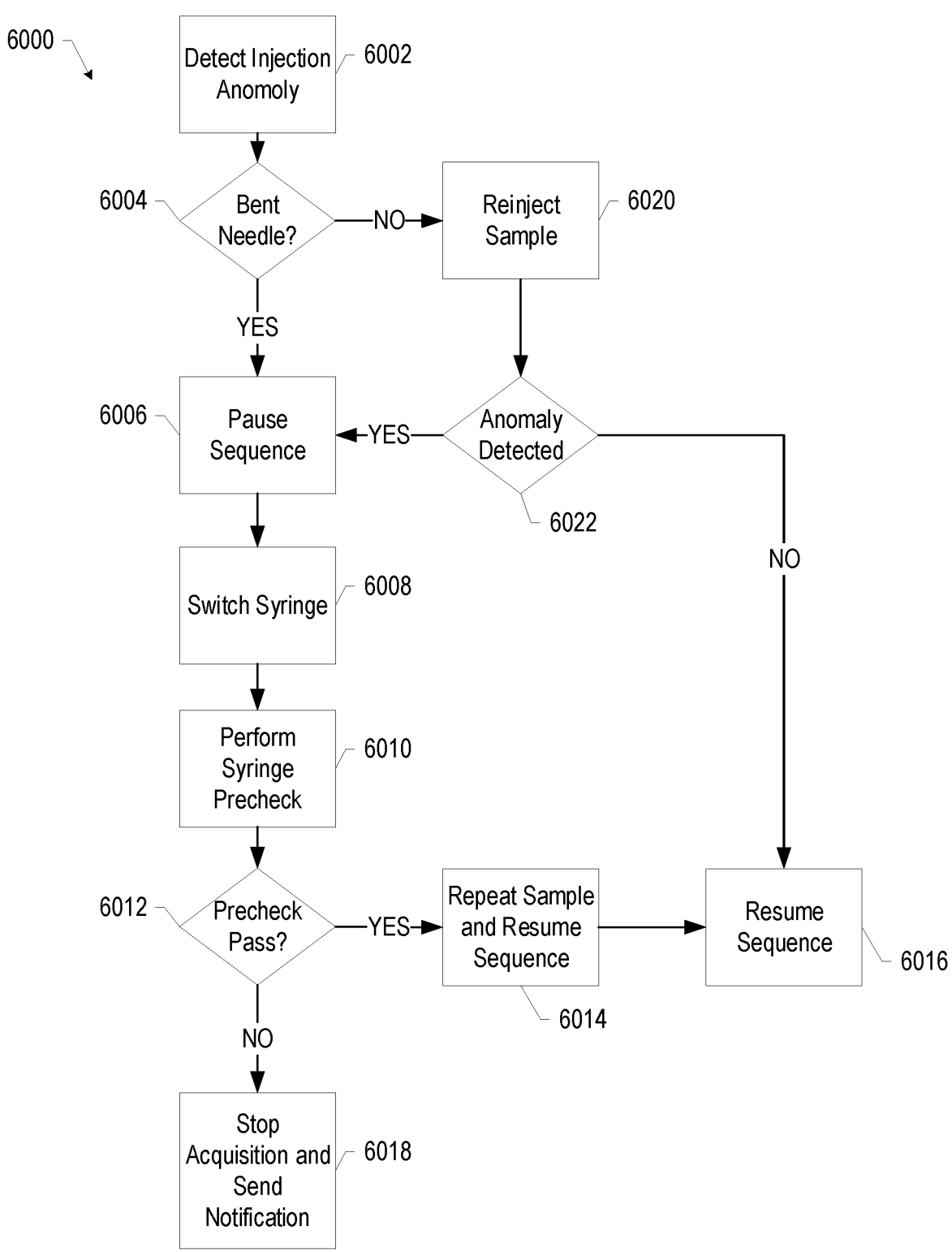
FIG. 6 is a flow diagram of an example method of performing support operations, in accordance with various embodiments.

FIG. 6 illustrates a method 6000 of changing a syringe. At 6002, an injection anomaly is detected. In various embodiments, the injection anomaly can be detected by analyzing the data generated from the analysis of the sample, such as a chromatogram or a mass spectrum. When there is a problem with sample injection that causes little or no sample to be injected, the peaks in the chromatogram or mass spectrum can be very small or non-existent. Thus, an injection anomaly can be detected by the absence of significant peak intensities. This can be detected by determined by comparing the peak intensifies to a threshold, such that if a mean peak intensity is below the threshold, the system can determine an injection anomaly has occurred.

At 6004, the system can determine is a needle or plunger of a syringe used for injecting the sample is bent or misaligned. In various embodiments, an image of the syringe and needle can be captured using an image capture device and analysis of the image can determine if the position of the needle tip is within tolerances. If the needle tip is outside of tolerances, such as too far to the left or right in the image, this can indicate the needle is not correctly inserting through a septum of the sample container or into an injection port of the system and the needle can be considered bent or otherwise damaged.

At 6006, if the needle is determined to be bent or damaged, the sequence of sample analyses can be paused. At 6008, the syringe can be switched out and a replacement syringe can be obtained. In various embodiments, this can happen without user intervention by instructing the autosampler to rotate a syringe carrier to position a new syringe in the active position or to place the damaged syringe in a syringe holder and pick up replacement syringe from another position on the syringe holder.

At 6010, a precheck of the syringe can be performed. In various embodiments, this can include determining a syringe plunger position, determining a needle depth, verifying the operation of the syringe such as by performing a wash step. Additionally, the precheck of the syringe can include verifying the location of the vials in the autosampler to ensure that no vials are missing.

At 6012, the system can determine if the syringe precheck is passed. At 6014, if the syringe precheck is passed, the system can repeat the sample and, at 6016, resume the sequence of sample analyses. Alternately, if the syringe precheck fails, at 6018, the system can notify the user and remain in the paused state.

Returning to 6004, when a bent needle or bent plunger is not detected, the injection anomaly may be caused by a clogged syringe or it may be a random error. At 6020, the system can reinject the sample and repeat the analysis. At 6022, the system can determine if the injection anomaly reoccurs of is corrected. If the injection anomaly is corrected and doesn't reoccur with the reinjection of the sample at 6018, the system can resume the sequence of sample analyses at 6016. Alternatively, detecting the anomaly again can be indicative of a clogged syringe, and the system can pause the sequence at 6006 in preparation of replacing the syringe.

In various embodiments, notifications and logging can occur at various times, including at 6002 when an injection anomaly is detected, at 6004 when a bent needle is detected at 6004, at 6012 when the syringe precheck passes or when the syringe precheck fails, and at any combination thereof. Notification can include sending one or more of an email, a text message, displaying a message on a user interface, sending a push notification to a portable device, and the like. Logging can include adding an entry to one or more of an audit log, a system log, and the like.

The invention claimed is:

1. A scientific instrument support apparatus, comprising:
   evaluation logic to detect an injection anomaly based on an evaluation of a chromatographic dataset and to identify a first syringe has a bent needle, a bent plunger, a blocked needle, or a stuck plunger;
   syringe logic to switch from the first syringe to a second syringe if it is identified that the first syringe has a bent needle, a bent plunger, a blocked needle, or a stuck plunger; and
   reporting logic to generate an entry in an event log or notify a user when there is a syringe problem,
   wherein at least one of the evaluation logic, the syringe logic, and the reporting logic are implemented by a computing device.

2. The scientific instrument support system of claim 1, wherein the evaluation logic, the syringe logic, and the reporting logic are implemented by a common computing device.

3. The scientific instrument support system of claim 1, wherein at least one of the evaluation logic, the syringe logic, and the reporting logic are implemented by a computing device remote from a scientific instrument.

4. The scientific instrument support system of claim 1, wherein at least one of the evaluation logic, the syringe logic, and the reporting logic are implemented in a scientific instrument.

5. The scientific instrument support system of claim 1, wherein the evaluation logic identifies the first syringe has a bent needle or a bent plunger based on image data.

6. The scientific instrument support system of claim 1, wherein the syringe logic further repeats an analysis of the sample when a bent needle or a bent plunger is not identified after the injection anomaly is detected.

7. The scientific instrument support system of claim 1, wherein the evaluation logic further includes pausing a sequence of sample analyses when the bent needle, the bent plunger, the blocked needle, or the stuck plunger is identified.

8. The scientific instrument support system of claim 1, wherein the syringe logic further includes performing a syringe precheck on the second syringe.

9. The scientific instrument support system of claim 8, wherein the reporting logic generates an entry in an event log or notifies the user if the syringe precheck fails or produces an error.

10. The scientific instrument support system of claim 8, wherein the syringe logic repeats analysis of a sample when the syringe precheck completes without errors.

11. The scientific instrument support system of claim 10, wherein the evaluation logic evaluates the chromatographic data set from the repeat analysis for a further injection anomaly.

12. The scientific instrument support system of claim 11, wherein the syringe logic resumes the sequence of sample analyses when the evaluation logic does not detect an injection anomaly during the repeat analysis.

13. The scientific instrument support system of claim 11, wherein the reporting logic further generates an entry in the event log or notifies the user when an injection anomaly is detected during the repeat analysis.

14. The scientific instrument support system of claim 8, wherein the syringe logic resumes the sequence of sample analyses after the syringe precheck completes without errors.

15. A method for scientific instrument support, comprising:

detecting an injection anomaly based on an evaluation of a chromatographic dataset;

identifying a first syringe has a bent needle, a bent plunger, a blocked needle, or a stuck plunger;

switching from the first syringe to a second syringe; and generating an entry in an event log or notifying a user of a syringe problem.

16. The method of claim 15, further including identifying the first syringe has a bent needle or a bent plunger based on image data.

17. The method of claim 15, further including ordering replacement syringes.

18. One or more non-transitory computer readable media having instructions thereon that, when executed by one or more processing devices of a scientific instrument support apparatus, cause the scientific instrument support apparatus to perform the method of claim 15.

* * * * *